(12) United States Patent
Ren et al.

(10) Patent No.: US 6,214,888 B1
(45) Date of Patent: Apr. 10, 2001

(54) DERMATOLOGICAL COMPOUNDS

(75) Inventors: Wu Yun Ren, Germantown; David A. Brown, Ellicott City, both of MD (US)

(73) Assignee: Applied Genetics Incorporated, Freeport, NY (US)

(*) Notice: Subject to any disclaimer, the term of this patent is extended or adjusted under 35 U.S.C. 154(b) by 0 days.

(21) Appl. No.: 09/086,547

(22) Filed: May 28, 1998

Related U.S. Application Data (63) Continuation of application No. PCT/US98/05346, filed on Mar. 18, 1998, which is a continuation-in-part of application No. PCT/US97/16642, filed on Sep. 18, 1997.
(60) Provisional application No. 60/048,597, filed on Jun. 4, 1997, provisional application No. 60/036,863, filed on Feb. 4, 1997, provisional application No. 60/035,947, filed on Jan. 21, 1997, and provisional application No. 60/026,577, filed on Sep. 18, 1996.

(51) Int. Cl.[7] .................................................. A61K 31/045
(52) U.S. Cl. ........................... 514/729; 568/819; 568/820
(58) Field of Search .................................. 568/819, 820; 514/729

(56) References Cited

U.S. PATENT DOCUMENTS

| | | |
|---|---|---|
| 3,956,361 | 5/1976 | Stephen . |
| 4,104,203 * | 8/1978 | Hall et al. ................................ 512/22 |
| 4,626,603 * | 12/1986 | Siegmeier et al. ...................... 568/833 |
| 4,647,585 | 3/1987 | Loots et al. . |
| 5,068,453 | 11/1991 | Kuwahara et al. . |
| 5,130,136 | 7/1992 | Shono et al. . |
| 5,352,440 * | 10/1994 | Gilchrest et al. ......................... 424/59 |
| 5,414,019 | 5/1995 | Gould et al. . |
| 5,532,001 * | 7/1996 | Gilchrest et al. ...................... 424/450 |
| 5,554,359 * | 9/1996 | Fuller ...................................... 424/59 |
| 5,574,195 | 11/1996 | Chastain et al. . |
| 5,587,402 | 12/1996 | Gould et al. . |
| 5,591,423 | 1/1997 | Fuller . |
| 5,602,184 | 2/1997 | Myers et al. . |
| 5,645,839 | 7/1997 | Chobanian et al. . |
| 5,698,184 | 12/1997 | Pickart . |
| 5,700,450 | 12/1997 | Gilchrest et al. . |
| 5,747,532 | 5/1998 | Lai . |
| 5,837,738 | 11/1998 | Williamson et al. . |
| 5,990,177 | 11/1999 | Brown . |

FOREIGN PATENT DOCUMENTS

| | | |
|---|---|---|
| 1 200 862 | 8/1970 | (GB) . |
| WO96/26711 | 9/1996 | (WO) . |
| WO 98/11882 | 3/1998 | (WO) . |

OTHER PUBLICATIONS

Merket et al, Chem. Abstracts, vol. 66, #94723a, 1967.*
Ishida et al, Chem. Abstracts, vol. 93, #89860w, 1980.*
Buchbauer et al, Chem. Abstracts, vol. 95, #115756e, 1981.*
Uchida et al, Chem. Abstracts, VGol. 112, #198816t, 1990.*
Kozlov et al, Chem. Abstracts, vol. 120, #77469p, 1994.*
Miftakhov et al, Chem. Abstracts, vol. 121, #157329d, 1994.*
Kemikubo et al, Chem. Abstracts, vol. 122, #265669u, 1995.*
Koval'skaya et al., Chem. Abstracts, vol. 125, #276201y. 1996.*
Adnot et al., "Pulmonary hypertension: NO therapy?," *Thorax,* 1996, 51:762–764.
Andersson and Stief, "Neurotransmission and the contraction and relaxation of penile erectile tissues," 1997, *World J. Urol.* 15:14–20 (abstract).
Andersson, K.–E., "Neurotransmitters and neuroreceptors in the lower urinary tract," *Curr. Opin. Obstet Gynecol.,* 1996, 8:361–365.
Baron, A., "Insulin and the Vasculature—Old Actors, New Roles," *J. Investig. Med.,* 1996, 44:406–412.
Barry, B. W. "Properties that Influence Percutaneous Absorption," *Dermatological Formulations: Percutaneous Absorption,* Marcel Dekker, Inc., New York, ,1983, pp. 127–233.
Barthelman et al., "Inhibitory Effects of Perillyl Alcohol on UVB–induced Murine Skin Cancer and AP–1 Transactivation," *Cancer Research,* Feb. 15, 1998, 58:711–716.
Baudouin et al., "Constitutive Nitric Oxide Synthase is Present in Normal Human Keratinocytes," *J. Invest. Dermatol.,* 1996, 106:428–431.
Brann et al., "Gaseous Transmitters and Neuroendocrine Regulation," *Neuroendocrinology,* 1997, 65:385–395.
Brown et al., "Aliphatic and Alicyclic Diols Induce Melanogenesis in Cultured Cells and Guinea Pig Skin," *J. Invest. Dermatol.,* 1998, 110:428–437.
Buchbauer et al., "Norbornanaverbindungen in der pharmazeutischen Forschung," *Pharmazie,* 1991, 46(Teil 1):88–97, and 46(Teil 2):116–170.
Carter et al., "Nitric oxide production is intensely and persistently increased in tissue by thermal injury," *Biochem. J.,* 1994, 304(Pt 1):201–04.
Cooke et al., "Nitric Oxide Synthase: Role in the Genesis of Vascular Disease," *Annu. Rev. Med.,* 1997, 48:489–509.
Crowell et al., "Chemoprevention of mammary carcinogenesis by hydroxylated derivatives of d–limonene," *Carcinogenesis,* 1992, 13:1261–1264.
Crowell et al., "Structure–activity relationships among monoterpene inhibitors of protein isoprenylation and cell proliferation," *Biochemical Pharmacology,* 1994, 47:1405–1415.
Dawson et al., "Nitric Oxide Actions in Neurochemistry," *Neurochem. Int.,* 1996, 29:97–110.

(List continued on next page.)

Primary Examiner—James H. Reamer
(74) Attorney, Agent, or Firm—Maurice M. Klee (57) ABSTRACT

The present invention relates to novel monocyclic and bicyclic monoterpene diols that stimulate melanogenesis in mammalian skin, hair, wool or fur, and, are useful for treating or preventing various skin and proliferative disorders, neurodegenerative diseases, and diseases regulated by the nitric oxide/cyclic GMP/protein kinase G pathway.

19 Claims, 1 Drawing Sheet

OTHER PUBLICATIONS

Gorfine, S., "Treatment of Benign Anal Disease with Topical Nitroglycerin," *Dis. Colon Rectum,* 1995, 38:453–456.

Haag et al., "Mammary carcinoma regression induced by perillyl alcohol, a hydroxilated analog of limonene," *Cancer Chemotherapy and Pharmacology,* 1994, 34:477–483.

He et al., "Isoprenoids Suppress the Growth of Murine B16 Melanomas In Vitro and In Vivo," *J. Nutr.,* 1997, 127:668–674.

Hidaka et al., "Isoquinolinesulfonamides, Novel and Potent Inhibitors of Cyclic Nucleotide Dependent Protein Kinase and Protein Kinase C," *Biochemistry,* 1984, 23, 5036–5041.

Jager et al., "Investigation of cytotoxic effects of 8 norbornane derivatives on 4 human cancer cell lines using the MTT assay," *Pharmazie,* 1995, 50:619–621.

Karlberg et al., "Hydroperoxides in oxidized *d*–limonene identified as potent contact allergens," *Arch. Dermatol. Res.,* 1994, 286:97–103.

Kitahara et al., "Evaluation of Skin Damage of Cyclic Monoterpenes, Percutaneous Absorption Enhancers, by Using Cultured Human Skin Cells," *Biol. Pharm. Bull.,* 1993, 16:912–916.

Kone, et al., "Biosynthesis and homeostatic roles of nitric oxide in the normal kidney," *Am. J. Physiol.,* 1997, 10:F561–578.

Lahera et al., "Nitric Oxide, the Kidney and Hypertension," *Am. J. Hypertens.,* 1997, 10:129–140.

Marriott and Higenbottam, "The role of nitric oxide in respiratory disease," 1997, *Schweiz Med. Wochenschr.* 127:709–714 (abstract).

Mashimo et al., "Effects of Vasodilators Guanethidine, Nicardipine, Nitroglycerin, and Prostaglandin $E_1$ on Primary Afferent Nociceptors in Humans," *J. Clin. Pharmacol.,* 1997, 37:330–335.

Miles et al., "Fluorometric Determination of Nitric Oxide," *Methods,* 1995, 7:40–47.

Murrell et al., "Modulation of tendon healing by nitric oxide," *Inflamm. Res.,* 1997, 46:19–27.

Ohmori et al., "Pharmacological Regulation on Melanogenesis," *Nippon Koshohin Kagakkaishi,* 1994, 18:215–219. English translation attached[1].

Packard et al., "Pathogenesis of Posttraumatic Headache and Migraine: A Common Headache Pathway?" *Headache,* 1997, Mar. 37:142–152.

Pipili–Synetos et al., "Inhibition of angiogenesis, tumor growth and metastasis by the NO–releasing vasodilators, isosorbide mononitrate and dinitrate," *Br. J. Pharmacol.,* 1995, 116:1829–1834.

Rishi et al., "Gastrointestinal Protection by NO from NSAIDS Induced Injury," *Indian J. Physiol. Pharmacol.,* 1996, 40:377–379.

Romero et al., "Involvement of Nitric Oxide and Cyclic GMP in Melanogenesis of Human Melanocytes," *J. Invest. Dermatol.,* 1996, 106:886.

Romero–Graillet et al., "Nitric Oxide Produced by Ultraviolet–irradiated Keratinocytes Stimulates Melanogenesis," *J. Clin. Invest.,* 1997, 99:635–642.

Romero–Graillet et al., "Ultraviolet B Radiation Acts through the Nitric Oxide and cGMP Signal Transduction Pathway to Stimulate Melanogenesis in Human Melanocytes," *J. Biol. Chem.* 1996, 271:28052–28056.

Rubbo et al, "Nitric Oxide Regulation of Tissue Free Radical Injury," *Chem. Res. Toxicol.,* 1996, 9:809–820.

Russin et al., "Inhibition of rat mammary carcinogenesis by monoterpenoids," *Carcinogenesis,* 1989, 10:2161–2164.

Samdani et al, "Nitric Oxide Synthase in Models of Focal Ischemia," *Stroke,* 1997, 28:1283–1288.

Schaffer et al., "Nitric Oxide Regulates Wound Healing," *J. Surg. Res.,* 1996, 63:237–240.

Schmidt et al., "Determination of Nitric Oxide via Measurement of Nitrite and Nitrate in Culture Media," 1995, *Biochemica* 2:22.

Shi et al., "Induction of differentiation in neuro–2A cells by the monoterpene perillyl alcohol," *Cancer Letters 95,* 1995, 1–6.

Shoff et al., "Concentration–dependent Increase of Murine P388 and B16 Population Doubling Time by the Acyclic Monoterpene Geraniol," *Cancer Research,* 1991, 41:37–42.

Smith and Reynard, 1992, Pharmacology, W. B. Saunders Co., Philadelphia, PA, pp. 626–31.

Suematsu et al., "Gaseous monoxides: a new class of microvascular regulator in liver," *Cardiovasc. Res.,* 1996, 32:679–686.

Thadani, U., "Nitrate Tolerance, Rebound, and their Clinical Relevance in Stable Angina Pectoris, Unstable Angina and Heart Failure," *Cardiovasc. Drugs,* 1997, 10:735–742.

Tooke et al, "Microvascular functional abnormalities in diabetes: the role of the endothelium," *Diabetes Res. Clin. Pract.,* 1996, 31Suppl:S127–S132.

Xie et al., "Activation of nitric oxide synthase gene for inhibition of cancer metastasis," *J. Leukoc. Biol.,* 1996, 59:797–803.

\* cited by examiner

FIG. 1

DERMATOLOGICAL COMPOUNDS

CROSS REFERENCE TO RELATED APPLICATIONS

This application is a continuation of PCT/US98/05346 filed Mar. 18, 1998, which is a continuation-in-part of PCT/US97/16642 filed Sep. 18, 1997, which is a continuation-in-part of application Ser. No. 60/026,577 filed Sep. 18, 1996, of application Ser. No. 60/035,947 filed Jan. 21, 1997, of application Ser. No. 60/036,863 filed Feb. 4, 1997, and of application Ser. No. 60/048,597 filed Jun. 4, 1997.

BACKGROUND OF THE INVENTION

1. Field of the Invention

The present invention relates to novel monocyclic and bicyclic monoterpene diols that stimulate melanogenesis in mammalian skin, hair, wool or fur, and, are useful for treating or preventing various skin and proliferative disorders, neurodegenerative diseases, and diseases regulated by the nitric oxide/cyclic GMP/protein kinase G pathway.

2. Description of Related Art

U.S. Pat. No. 5,352,440 is directed to increasing melanin synthesis in melanocytes and increasing pigmentation by administration of certain diacylglycerol compounds.

U.S. Pat. No. 5,532,001 is directed to increasing pigmentation in mammalian skin via administration of certain DNA fragments.

U.S. Pat. No. 5,554,359 is directed to increasing levels of melanin in melanocytes by administration of lysosomotropic agents.

SUMMARY OF THE INVENTION

In one aspect, the present invention is directed to compounds having the structure:

wherein

A is a substituted or unsubstituted cyclic terpene;

$R_1$, $R_2$, $R_8$ and $R_9$ are all —OH; and $R_3$, $R_4$, $R_5$, $R_6$, $R_7$ and $R_{10}$ are each independently hydrogen, or a linear or branched, cyclic, bicyclic or polycyclic group containing from one atom to fifty atoms, at least one of which is carbon, nitrogen, oxygen, or sulfur.

Another aspect of the present invention concerns stimulation of melanogenesis in mammalian skin, hair, wool or fur, by administering to a locus in need of such stimulation an effective amount of one or more of the compounds described above.

Another aspect of the present invention concerns treatment of proliferative, tumorous or cancerous disorders in mammals, including but not limited to such conditions of a dermatological nature, by administering to a mammal in need of such treatment an effective amount of one or more of the compounds described above.

A further aspect of the present invention concerns treatment of neurodegenerative disorders or nerve damage in mammals by administering to a mammal in need of such treatment an effective amount of one or more of the compounds described above.

Another aspect of the present invention concerns treatment of diseases regulated by the nitric oxide/cyclic GMP/protein kinase G pathway in mammals by administering to a mammal in need of such treatment an effective amount of one or more of the compounds described above.

DETAILED DESCRIPTION OF THE INVENTION

The compounds of the present invention have the structures described above. Preferably, the A cyclic terpene portion is monocyclic or bicyclic, more preferably bicyclic. Most preferably, A is a substituted or unsubstituted moiety having the skeleton of (+) or (−)-camphenes; (+) or (−)-camphor; (−)-β-pinenes and 2- or 3-carenes; (−)-myrtenol or (−)-myrtanol; or (−)-verbenol or (−)-verbenone and their derivatives, some of which are shown below.

As mentioned above, $R_3$, $R_4$, $R_5$, $R_6$, $R_7$ and $R_{10}$ are each independently hydrogen, or a linear or branched, cyclic, bicyclic or polycyclic group containing from one atom to fifty atoms, at least one of which is carbon, nitrogen, oxygen, or sulfur. Those R groups include linear or branched alkyl, particularly $C_1$–$C_6$ alkyl, linear or branched alkenyl, linear or branched alkynyl, cycloalkyl, aryl, aralkyl, polynuclear groups such as tetralin, decalin or pyrene, and heterocyclic groups containing nitrogen, sulfur and/or oxygen, such as pyrrole, furan, thiophene, imidazole, oxazole, thiazole, pyrazole, 3-pyrroline, pyridine, pyrimidine, purine, quinoline, isoquinoline or carbazole. Any of the foregoing groups may be optionally substituted with groups such as halogens, amino, nitro, hydroxyl or sulfhydryl.

Regarding the non-cyclic terpene backbone portion of the present compounds, they preferably have one of the structures shown immediately below:

wherein R is hydrogen or methyl.

Particularly preferred compounds include (−)-2,2-dimethyl-3-hydroxy-3-hydroxymethyl-norbornane; (+)-2,2-dimethyl-3-hydroxy-3-hydroxymethyl-norbornane; (−)-2,2-dimethyl-3-(2,3-dihydroxy-propan-3-yl)-norbornane; and (+)-2,2-dimethyl-3-(2,3-dihydroxy-propan-3-yl)-norbornane.

The present invention is based on the unique observation that the present compounds effectively and efficiently induce melanogenesis in mammalian cells, which has several consequences. First, increasing melanogenesis leads to increasing the melanin content of melanocytes, and hence results in increased pigmentation or darkened color of the skin, hair wool or fur. Thus, the present invention is useful in the treatment of hypopigmentation disorders, such as albinism, vitiligo, etc. It is also believed that increasing the pigmentation of skin according to the present invention will protect such skin from subsequent UV light damage, sunburn, photoaging and development of skin cancers. Finally, since the methods and compositions described herein induce differentiation of a melanoma cell line, the present invention may be used to treat hyperproliferative disorders such as actinic keratosis, basal cell carcinoma, squamous cell carcinoma, fibrous histiocytoma, dermatofibrosarcoma protuberans, hemangioma, nevus flammeus, xanothoma, Kaposi's sarcoma, mastocytosis, mycosis fungoides, lentigo, nevocellular nevus, lentigo maligna, malignant melanoma, and metastatic carcinoma.

The present methods and compositions are also useful in the treatment of diseases characterized by inflammation and disturbance of keratinization, including psoriasis vulgaris, psoriasis eosinophilia, acne vulgaris, acne conglobata, acne fulminans, osteoma cutis, nodulocystic acne, cystic acne and benign and premalignant dermatoses.

The compounds also effectively and efficiently increase differentiation of neuronal cells, including increased neuronal dendricity and neuronal tyrosine hydroxylase activity, which has several consequences. First, increasing dendricity leads to increased neuronal communication, thereby increasing neuronal function and performance. Thus, the present invention is useful for treating diseases or disorders marked by reduction of neuronal dendricity and function, including but not limited to Parkinson's disease, amyotrophic lateral sclerosis, Alzheimer's disease, or any other neurodegenerative disease, or physical or toxic damage to brain, spinal or peripheral nerve cells. Further, the present invention is useful for restoring or optimizing neuronal communication, function or performance.

Second, increasing tyrosine hydroxylase activity directly increases dopamine synthesis. Thus, the present invention is particularly useful for treating Parkinson's disease which is specifically marked by depletion of dopamine synthesis.

Third, induction of neuronal differentiation reverses neuronal proliferative disorders. Thus, the present invention is useful for treating neuronal proliferative, tumorous, or cancerous disorders, or said disorders in any other cell type that might be similarly affected.

Finally, since the methods and compositions described herein induce differentiation, dendricity and tyrosine hydroxylase in a neuronal cell model, the present invention is useful for treating additional neurodegenerative disorders or neuropathies including but not limited to diffuse cerebral cortical atrophy, Lewy-body dementia, Pick disease, mesolimbocortical dementia, thalamic degeneration, Huntington chorea, cortical-striatal-spinal degeneration, cortical-basal ganglionic degeneration, cerebrocerebellar degeneration, familial dementia with spastic paraparesis, polyglucosan body disease, Shy-Drager syndrome, olivopontocerebellar atrophy, progressive supranuclear palsy, dystonia musculorum deformans, Hallervorden-Spatz disease, Meige syndrome, familial tremors, Gilles de la Tourette syndrome, acanthocytic chorea, Friedreich ataxia, Holmes familial cortical cerebellar atrophy, Gerstmann-Straussler-Scheinker disease, progressive spinal muscular atrophy, progressive balbar palsy, primary lateral sclerosis, hereditary muscular atrophy, spastic paraplegia, peroneal muscular atrophy, hypertrophic interstitial polyneuropathy, heredopathia atactica polyneuritiformis, optic neuropathy, and ophthalmoplegia.

It has also been discovered that the present class of compounds stimulate cellular nitric oxide synthesis and have their action blocked by scavengers of nitric oxide (NO), and by inhibitors of cyclic guanosine monophosphate (cGMP) or inhibitors of cGMP-activated protein kinase (PKG). This indicates that these compounds act via the NO/cGMP/PKG signal transduction pathway. Unlike previous compounds like nitroglycerin and isosorbide dinitrate that stimulate this pathway by releasing NO upon reaction with intracellular sulfhydryl groups (Smith and Reynard, 1992, Pharmacology, W.B. Saunders Co., Philadelphia, Pa., pp. 626–31), the compounds of this invention appear to act by direct stimulation of nitric oxide synthase (NOS) activity, thus generating NO de novo. Whereas depletion of intracellular sulfhydryl groups rapidly leads to tolerance and ineffectiveness of nitroglycerin and related compounds (Smith and Reynard, 1992), tolerance will not be acquired to the compounds of the present invention since they do not require the presence of sulfhydryl groups for generation. Thus, it is contemplated that the compounds of the present invention will provide a preferred alternative method of treatment for conditions presently treated by NO donors.

Both clinical application and research studies have demonstrated that stimulation of the NO/cGMP/PKG pathway is useful for treatment of:

(i) heart disease including stable angina pectoris, unstable angina, myocardial infarction, and myocardial failure associated with myocardial ischemia, atherosclerosis, vascular hypertrophy, and thrombosis (Cooe and Dzau, 1997, *Annu. Rev. Med.* 48:489–509; Thadani, 1997, *Cardiovasc. Drugs* 10:735);

(ii) hypertension (Cooe and Dzau, 1997);

(iii) stroke (Samdani, et al., 1997, Stroke 28:1283–1288);

(iv) primary pulmonary hypertension, chronic obstructive pulmonary disease, and adult respiratory distress syndrome (Adnot and Raffestin, 1996, *Thorax* 51:762–764; Marriott and Higenbottam, 1997, *Schweiz Med. Wochenschr.* 127:709–714);

(v) microvascular functional abnormalities in diabetes that link insulin-resistance to hypertension, thrombosis and atherosclerosis (Tooke, et al., 1996, *Diabetes Res. Clin. Pract.* 31Suppl:S127–S132; Baron, 1996, *J. Investig. Med.* 44:406–412);

(vi) hemostatic irregularities of glomerular vascular and tubular function with consequences for development of hypertension (Kone and Baylis, 1997, *Am. J. Physiol.* 10:F561–578; *Am. J. Hypertens.* 10:129–140);

(vii) microvascular irregularities in the liver with consequences for biliary transport and tissue regeneration (Suematsu, et al., 1996, *Cardiovasc. Res.* 32:679–686);

(viii) disorders of bladder function and reflex relaxation for micturition (Andersson, 1996, *Curr. Opin. Obstet. Gynecol.* 8:361–365);

(ix) disorders of neurotransmitter release, neuron morphogenesis, synaptic plasticity, and neuroendocrine regulation (Dawson and Dawson, 1996, *Neurochem. Int.* 29:97–110; Brann, et al., 1997, *Neuroendocrinology* 65:385–395);

(x) regional pain including migraine headaches (Mashimo, et al., 1997, *J. Clin. Pharmacol.* 37:330–335; Packard and Ham, 1997, Mar. 37:142–152);

(xi) gastrointestinal protection from non-steroidal anti-inflammatory drugs (Rishi, et al., 1996, *Indian J. Physiol. Pharmacol.* 40:377–379);

(xii) benign anal disease (Gorfine, 1995, *Dis. Colon Rectum* 38:453–456);

(xiii) impotence (Andersson and Stief, 1997, *World J. Urol.* 15:14–20);

(xiv) regulation of tissue free radical injury (Rubbo, et al., 1996, *Chem. Res. Toxicol.* 9:809–820); and (xv) inhibition of tumor growth, tumor apoptosis, angiogenesis, and metastasis (Pipili-Synetos, et al., 1995, *Br. J. Pharmacol.* 116:1829–1834; Xie, et al., 1996, *J. Leukoc. Biol.* 59:797–803); and (xvi) stimulation of wound healing including cuts, tendon injury and thermal injury (Schaffer, et al., 1996, *J. Surg. Res.* 63:237–240; Murrell, et al., 1997, *Inflamm. Res.* 46:19–27; Carter, et al., 1994, *Biochem. J.* 304(Pt 1):201–04).

In addition, the NO/cGMP/PKG pathway mediates melanogenesis induced by ultraviolet light (Romero-Graillet, et al., 1996, *J. Biol. Chem.* 271:28052–28056; Romero-Graillet, et al., 1997, *J. Clin. Invest.* 99:635–642) and aliphatic and alicyclic diols (U.S. patent application Ser. No. 08/933,143, entitled "Dermatalogical Compositions and Methods" filed Sep. 18, 1997).

The present invention contemplates the use of one or more of the above-mentioned compounds as an active ingredient for various uses. In a preferred embodiment, the active ingredient(s) is combined with an acceptable carrier to form a topical formulation which may be placed on the skin for dermatological uses. Topical formulations may include ointments, lotions, pastes, creams, gels, drops, suppositories, sprays, liquids, shampoos, powders and transdermal patches. Thickeners, diluents, emulsifiers, dispersing aids or binders may be used as needed. Preferably, one function of the carrier is to enhance skin penetration of the active ingredient(s), and should be capable of delivering the active ingredient(s) to melanocytes under in vivo conditions. Suitable carriers are well known to one of ordinary skill, and include liposomes, ethanol, dimethylsulfoxide (DMSO), petroleum jelly (petrolatum), mineral oil (liquid petrolatum), water, dimethylformamide, dekaoxyethylene-oleylether, oleic acid, 2-pyrrolidone and Azone® brand penetration enhancer (Upjohn). A particularly preferred composition includes an active ingredient(s) as described above, with one of 2-pyrrolidone, oleic acid and/or Azone® as penetration enhancer, solubilized in a base of water, ethanol, propanol and/or propylene glycol (the latter component having properties of a carrier, penetration enhancer and an active ingredient as described herein). Depending on the specific application, the compositions of the present invention may also include other active ingredients, as well as inert or inactive ingredients.

Particularly preferred formulations include an active ingredient(s) in conjunction with one or more melanogenesis-enhancing agents such as α-hydroxy acids, salts and derivatives thereof; α-keto acids, salts and derivatives thereof; β-hydroxy acids, salts and derivatives thereof; retinoids, salts and derivatives thereof; Vitamin A and related compounds; acids; phenol; and methoxypropyl-gluconamide, as more fully described in co-pending application Ser. No. 09/055,274 filed Apr. 6, 1998 entitled "Dermatological Formulations and Methods", the contents of which are incorporated herein by reference.

The dose regimen will depend on a number of factors which may readily be determined, such as severity and responsiveness of the condition to be treated, but will normally be one or more doses per day, with a course of treatment lasting from several days to several months, or until a cure is effected or a diminution of disease state is achieved, or a cosmetically desired degree of melanogenesis (tanning) is achieved, depending on the application. One of ordinary skill may readily determine optimum dosages, dosing methodologies and repetition rates. In general, it is contemplated that topical formulations (such as creams, lotions, solutions, etc.) will have a concentration of active ingredient of from about 0.01% to about 50%, preferably from about 0.1% to about 10%. In general, it is contemplated that unit dosage form compositions according to the present invention will contain from about 0.01 mg to about 100 mg of active ingredient, preferably about 0.1 mg to about 10 mg of active ingredient.

The methods and compositions of the present invention also contemplate the use of one or more of the above-mentioned compounds as an active ingredient to stimulate neuronal differentiation, dendricity, and/or tyrosine hydroxylase activity (with resultant increased dopamine synthesis) and/or to treat disease conditions related to the NO/cGMP/PKG pathway. In a preferred embodiment, the active ingredient(s) is given orally, intravenously, or transdermally in an acceptable formulation. A particularly preferred carrier for some formulations is 1,2-propylene glycol since it is an excellent solvent for certain compounds in this invention. Additionally, 1,2-propylene glycol as carrier has itself, as described in this invention, similar but lesser activity than the preferred active ingredient(s). Depending on the specific application, the compositions of the present invention may also include other active ingredients, as well as inert or inactive ingredients.

The dose regimen will depend on a number of factors which may readily be determined, such as severity and responsiveness of the condition to be treated, but will normally be one or more doses per day, with a course of treatment lasting from several days to several months, or until a cure is effected or a diminution of disease state is achieved. One of ordinary skill may readily determine optimum dosages, dosing methodologies and repetition rates. In general, it is contemplated that unit dosage form compositions according to the present invention will contain from about 0.01 mg to about 100 mg of active ingredient, preferably about 0.1 mg to about 10 mg of active ingredient. Topical formulations (such as creams, lotions, solutions, etc.) may have a concentration of active ingredient of from about 0.01% to about 50%, preferably from about 0.1% to about 10%.

Another aspect of the present invention is based on the observation that the subject compounds which stimulate melanin production act via the Nitric Oxide/cyclic Guanosine monophosphate/Protein Kinase G ("NO/cGMP/PKG") pathway. Thus, the present invention includes not only the compounds described above, but any compound which acts via the NO/cGMP/PKG pathway to stimulate melanin synthesis by increasing cellular production of NO, cGMP or PKG. Conversely, agents which decrease cellular production of NO, cGMP or PKG will decrease or suppress melanin production and pigmentation in mammalian skin, hair, fur or wool, and the present invention is also directed to those compositions and methods. Such is useful in, for example, the lightening of skin, hair, wool or fur for cosmetic purposes, or the treatment of hyperpigmentation or uneven pigmentation disorders such as vitiligo, dermal melanocytosis, Franceschetti-Jadassohn Syndrome, etc. For such depigmentation applications, the formulation and dosing would be as described above with respect to pigmentation applications.

Discovery of the pathway through which the present compounds act also leads to methods for screening compounds for melanogenic activity and potency, or for their ability to reduce or suppress melanogenesis, based on measurement of generation of nitric oxide (NO) or measurement of nitric oxide synthesis (NOS) activity. Methods for measurement of NO or NOS include but are not limited to the following well known methods. Measurement of NO is usually based on the fact that NO rapidly decomposes to nitrate and nitrite in aqueous solution. Nitrate reductase is added to culture media or cell extracts to ensure complete conversion of nitrate to nitrite. Griess reagents (sulfanilamide and N-[1-naphthyl]-ethylenediamine) are then added to convert nitrite into a deep purple azo compound that absorbs maximally at 540 nm (Schmidt, et al., 1995, *Biochemica* 2:22). Reactions are typically carried out in a 96-well format with absorbances read on a microtiter plate reader. Alternatively, following conversion of nitrate to nitrite as described above, DAN reagent (2,3-diaminonaphthalene) is added followed by NaOH which converts nitrite into the fluorescent compound 1(H)-naphthotriazole. This is measured fluorimetrically with excitation at 365 nm and emission at 450 nm, typically in a 96-well format (Miles, et al., 1995, *Methods* 7:40). NOS activity is measured by adding [$^3$H]-arginine to intact tissues or protein extracts, and measuring release of $^3$H resulting from the conversion of arginine to citrulline during the enzymatic formation of NO by NOS (Baudouin and Tachon, 1996, *J. Invest. Dermatol.* 106:428–431). Alternatively, the production of cGMP or activity of PKG can be used as a screening tool. cGMP may be measured by commercially available immunoassay (see Romero-Graillet, et al., 1996,*J. Biol. Chem.* 271:28052–28056). PKG may be measured by cyclic GMP dependent kination of a primary histone target (see Hidaka, et al., *Biochemistry* 1984, 23, 5036–5041)

Compounds according to the present invention may be synthesized in a number of ways known to one of ordinary skill. For example, a series of novel monocyclic and bicyclic monoterpenoid 1,2-diol derivatives (1a,b–6a,b below) may be synthesized from (+) or (−)-camphenes, (+) or (−)-camphor, (−)-β-pinenes, 2- or 3-carenes, (−)-myrtenol, (−)-verbenol and their derivatives.

The syntheses of the structures described above are initiated using chirally pure naturally occurring bicyclic (+) or (−)-camphenes, (+) or (−)-camphor, (−)-β-pinenes, 2 or 3-carenes, (−)-myrtenol, or (−)-verbenol as core chiral units. An enantiomerically controlled construction method is used to synthesize novel compounds that are exemplified herein by (+) and (−)-2,2-dimethyl-3-hydroxy-3-hydroxy-methyl-norbornane, and, (+) and (−)-2,2-dimethyl-3-(2,3-dihydroxy-propan-3-yl)-norbornane.

The one step syntheses of (+)- and (−)-1b and 3b are accomplished by cis-hydroxylation of (+) and (−)-camphene and (−)-β-pinene with osmium tetroxide and hydrogen peroxide or N-methylmorpholine N-oxide in t-butanol. The same technology may be applied to (+) and (−)-camphor and (−)-verbenone; in that case a Wittig reaction is used to convert the ketone to the corresponding olefin, and then the above described cis-hydroxylation is done to give 2b and 4b. For 2- and 3-carenes a hydroboration is done to generate alcohols, which are then oxidized to the corresponding ketones. The Wittig reaction is then used to convert the ketones to olefins, which give 5b and 6b following cis-hydroxylation as described above.

The synthesis of (+) or (−) 1a to 6a are achieved in four-steps from (+) or (−)-camphene and (−)-β-pinene and corresponding olefins of (+) or (−)-camphor, (−)-verbenone or 2- or 3-carene prepared as described above. Hydroboration of olefinic 1a to 6a or (−)-myrtenol gives the corresponding 3-exo alcohols, which are then oxidized with pyridinium dichromate to their respective aldehydes. Treatment of the aldehydes with (ethyl)triphenylphosphonium halide or respective corresponding (alkyl) triphenylphosphonium halide affords corresponding (2-propen-3-yl)-monoterpenes. Cis-hydroxylation of these (2-propen-3-yl)-monoterpenes furnishes the synthesis of 1a–6a.

The following examples are illustrative of the processes and products of the present invention, but are not to be construed as limiting. The examples which follow make reference to structures I–VI; those structures are depicted immediately below.

EXAMPLE 1
Synthesis of (+) and (−)-2,2-dimethyl-3-hydroxy-3-hydroxymethyl-norbornanes (II)

To an ice cooled mixture of (+) or (−)-camphene I (20 g, 0.15 mole) in 200 ml of tert-butyl alcohol were added 30% hydrogen peroxide in water (17 ml, 0.15 mole) and 125 mg of osmium tetroxide as catalyst. The mixture was stirred and temperature maintained at 0° C. in a ice bath for 4 hours and then at room temperature for 20 hrs. A slurry of 5 g of magnesium silicate, 500 mg of sodium hydrogen sulfite, and 20 ml of water was added, and the magnisol was filtered. The filtrate was concentrated and the residue was added to methylene chloride. The methylene chloride solution was washed with brine twice, dried over $MgSO_4$ and evaporated to dryness. Column chromatography of the crude mixture over a silica gel column eluted with 50:1 $CH_2Cl_2:CH_3OH$ gave pure II (1.8 g from (−)-camphene and 1 g from (+)-camphene) as crystalline solid. The NOE difference spectrum of II showed a NOE signal increase of methylene side chain protons (3.64 ppm) upon irradiation of H-7 proton (1.62 ppm). This evidence strongly suggests 3-hydroxymethylation of (+) or (−)-II at the exo-position.

EXAMPLE 2
Synthesis of (+) and (−)-2,2-dimethyl-3-hydroxymethyl-norbornanes (III)

A reaction mixture of (+) or (−)-camphene I (70 g, 0.5 mole) in 500 ml of 2-methoxyethyl ether was stirred at room temperature and under a blanket of slight positive atmospheric nitrogen pressure. To this was added dropwise a 1M $B_2H_6$-THF complex (167 ml) over a period of 15 minutes. The reaction mixture was heated at 80° C. (oil bath temperature) overnight, and then cooled to ice bath temperature. A 800 ml 4N NaOH solution was added dropwise followed by 70 ml of 30% $H_2O_2$. The reaction mixture was then extracted with diethyl ether twice (500 ml each), dried over $Na_2SO_4$ and the low boiling point solvents were evaporated. The high boiling point 2-methoxyethyl ether was removed by high vacuum distillation and the crystalline solid residue of III was collected (63 g for (+)-I and 67 g for (−)-I). The 1H nmr spectrum showed two proton multiple peaks at 3.5 ppm for methylene protons of side chain (the NOE difference spectrum of III showed that the increase of the NOE signal of methylene side chain protons (3.5 ppm) upon irradiation of H-7 proton (1.56 PPM). This evidence suggests that 3-hydroxymethyl group was at the exo-position of the norbornane ring.

EXAMPLE 3
Synthesis of (+) and (−)-2,2-dimethyl-3-formylmethyl-norbornanes (IV)

To a stirred reaction mixture of (+) or (−)-2,2-dimethyl-3-hydroxymethyl-norboranes III (20 g, 0.13 mole) in 800 ml of dichloromethane was added 58.6 g (0.15 mole) of pyridium dichromate. The reaction mixture was stirred at room temperature for 36 hours. The dark slurry reaction mixture was purified by passing through a short silica gel column eluted with dichloromethane. The collected fractions were concentrated under vacuum to give IV in quantitative yield which was used without further purification.

EXAMPLE 4
Synthesis of (+) and (−)-2,2-dimethyl-3-(2-propen-3-yl)-norbornanes (V)

Sodium hydride (3.35 g, 0.14 mole) was added to DMSO under nitrogen and the resulting suspension was heated at 80° C. until the solution was clear and the evolution of hydrogen ceased. The resulting solution of methylsulfinyl carbanion was cooled in a ice bath, and (ethyl)triphenyl-phosphonium iodide (58.6 g, 0.14 mole) was added to give a deep orange color mixture. The ice bath was removed and the reaction mixture was stirred at least 10 minutes at room temperature before the aldehyde IV (20 g, 0.12 mole) in 20 ml DMSO was added. The reaction mixture was kept at room temperature overnight, and then was poured into 400 ml of water. The aqueous phase was extracted three times with 500-, 300- and 150-ml portions of n-hexanes. The combined n-hexane layer was dried over $MgSO_4$ and evaporated to dryness. The residue was distilled in vacuo to give V (14.5 g for (+)-V and 16 g for (−)-V). The 1H nmr spectrum showed two olefinic protons as a multiplet at 5.5 ppm and one methyl group as a multiplet at 1.6 ppm. The broadband proton decoupling spectrum of V showed twelve peaks with two peaks at 125 and 130 ppm specific for olefinic carbons.

EXAMPLE 5
Synthesis of (+) and (−)-2,2-dimethyl-3-(2,3-dihydroxy-propan-3-yl)-norbornanes (VI)

To an ice cooled mixture of (+) or (−)-V (10 g, 0.06 mole for (+)-v or 13 gm, 0.08 mole for (−)-V) in 150 ml of tert-butyl alcohol were added 30% hydrogen peroxide in water (8 ml for (+)-V and 9.1 ml for (−)-V) and 125 mg of osmium tetroxide as catalyst. This mixture was stirred and maintained at 0° C. in a ice bath for 4 hours, and then at room temperature for 20 hrs. A slurry of 5 g of magnesium silicate, 500 mg of sodium hydrogen sulfite, and 20 ml of water was added, and the magnisol was filtered. The filtrate was concentrated and the residue was added to methylene chloride. The methylene chloride solution was washed with brine twice, dried over $MgSO_4$ and evaporated to dryness. Column chromatography of the crude mixture over silica gel eluted with 50:1 $CH_2Cl_2$:$CH_3OH$ gave pure VI (1.82 g from (−)-V and 2 g from (+)-V) as an oily liquid.

EXAMPLE 6
Induction of melanogenesis in S91 mouse melanoma cells by (+) and (−)-2,2-dimethyl-3-hydroxy-3-hydroxymethyl-norbornanes (II), (+) and (−)-2,2-dimethyl-3-hydroxymethyl-norbornanes (III), and, (+) and (−)-2,2-dimethyl-3-(2,3-dihydroxy-propan-3-yl)-norbornanes (VI)

Cloudman S91 mouse melanoma cells were obtained from ATCC and cultured in MEM (BioWhittaker) with 10% calf serum (BioWhittaker or HyClone). Cells were plated at $0.1 \times 10^6$ cells/well (~50% plating efficiency=$0.05 \times 10^6$ viable cells/well) in 6-well plates the day before treatments, in media containing 10% calf serum. Media was changed to MEM with 2% calf serum concomitant with addition of treatments. Treatments were dissolved in ethanol as 0.5M solutions which was added in appropriate volumes directly to cell culture media (Brown, et al., 1998, *J. Invest. Dermatol.* 110:48–437).

Six days later, cells were examined microscopically, and the percentage of differentiated (multipolar) cells was estimated by counting random fields. Cells were then trypsinized, counted, pelleted and analyzed for tyrosinase activity. Cellular pellets were solubilized by sonicating for 5 seconds in 600 ul 50 mM phosphate buffer pH 6.8 containing 0.5% Triton-X100, followed by vortexing, incubation on ice for 30 min, and then revortexing. From this, 200 ul aliquots were combined with 200 ul of reaction mixture containing either 75 uM tyrosine, 75 uM L-Dopa, and 2 uCi L-[3,5-3H]Tyrosine in 50 mM NaPO4 pH 6.8 (L-Dopa +), or, 75 uM tyrosine, and 2 uCi L-[3,5-3H]Tyrosine in 50 mM NaPO4 pH 6.8 (L-Dopa −), and then incubated 1 hr at 37° C. Reactions were stopped by addition of 400 ul 10% activated charcoal in 0.1N HCl and incubation on ice for 15 min. This mixture was centrifuged at 17,300×g for 5 min, and 400 ul supernatant was then filtered through a 0.22 uM GV Durapore centrifugal filter unit (Millipore) by centrifuging at 17,300×g for 5 min. Filtrate was added to 4 ml Fisher Plus scintillation fluid and counted on a Hewlett Packard 2000A scintillation counter. Tyrosinase activity was calculated as dpm/hr/103 cells. Each sample was analyzed with and without L-Dopa, a necessary cofactor for tyrosinase; all reported tyrosinase values are exclusive of counts that occurred in buffer blanks and L-dopa negative aliquots (Brown, et al., 1998, *J. Invest. Dermatol.* 110:48–437)

TABLE 1

|  | Cells (× 10⁶) | % Multi-Polar | Tyrosinase dpm/hr/103 | Tyrosinase Induction |
|---|---|---|---|---|
| Control | 0.674 | 5% | 373 | 1.0× |
| 100 uM I | 0.752 | 10% | 804 | 2.2× |
| 500 uM I | 0.359 | 50% | 2070 | 5.5× |
| 1000 uM I | 0.193 | 75% | 4129 | 11.1× |

TABLE 1-continued

|  | Cells (× 10⁶) | % Multi-Polar | Tyrosinase dpm/hr/103 | Tyrosinase Induction |
|---|---|---|---|---|
| 2500 uM I | 0.079 | 100% | 11295 | 30.3× |
| 50 uM II− | 0.433 | 20% | 1091 | 2.9× |
| 100 uM II− | 0.339 | 35% | 1524 | 4.1× |
| 500 uM II− | 0.279 | 50% | 1880 | 5.0× |
| 1000 uM II− | 0.154 | 75% | 2735 | 7.3× |
| 50 uM II+ | 0.334 | 50% | 1255 | 3.4× |
| 100 uM II+ | 0.118 | 75% | 3724 | 10.0× |
| 500 uM II+ | 0.076 | 100% | 7922 | 21.3× |
| 1000 uM II+ | 0.049 | 100% | 5767 | 15.5× |
| 100 uM III− | 0.694 | 25% | 825 | 2.2× |
| 500 uM III− | 0.185 | 100% | 1680 | 4.5× |
| 1000 uM III− | 0.153 | 100% | 3070 | 8.2× |
| 2500 uM III− | 0.098 | 100% | 4284 | 11.5× |
| 50 uM III+ | 0.634 | 10% | 699 | 1.9× |
| 100 uM III+ | 0.357 | 35% | 1626 | 4.4× |
| 500 uM III+ | 0.306 | 75% | 2432 | 6.5× |
| 1000 uM III+ | 0.142 | 100% | 3461 | 9.3× |
| 50 uM VI− | 0.216 | 75% | 1429 | 3.8× |
| 100 uM VI− | 0.189 | 75% | 3001 | 8.0× |
| 250 uM VI− | 0.186 | 100% | 5396 | 14.5× |
| 50 uM VI+ | 0.667 | 25% | 1285 | 3.4× |
| 100 uM VI+ | 0.394 | 50% | 1444 | 3.9× |
| 500 uM VI+ | 0.108 | 100% | 4200 | 11.3× |
| 1000 uM VI+ | 0.044 | 100% | 7630 | 20.5× |
| 50 uM VII | 0.434 | 25% | 593 | 1.6× |
| 100 uM VII | 0.485 | 25% | 516 | 1.4× |
| 250 uM VII | nonadherent | | | |

I: (1R,2R,3S,5R)-(−)-pinanediol
II−: (−)-2,2-dimethyl-3-hydroxy-3-hydroxymethyl-norbornane
II+: (+)-2,2-dimethyl-3-hydroxy-3-hydroxymethyl-norbornane
III−: (−)-2,2-dimethyl-3-hydroxymethyl-norbornane
III+: (+)-2,2-dimethyl-3-hydroxymethyl-norbornane
VI−: (−)-2,2-dimethyl-3-(2,3-dihydroxy-propan-3-yl)-norbornane
VI+: (+)-2,2-dimethyl-3-(2,3-dihydroxy-propan-3-yl)-norbornane
VII: 3-ethyl-2-aldehyde-pinane Treatment of S91 cells showed that the compounds of this invention induce significant melanogenic activity, and are more potent than one of the most active compounds [(1R, 2R,3S,5R)-(−)-pinanediol] described in co-pending application PCT/US98/05346. For example, only 100 uM II+ was required to induce a 10-fold increase of tyrosinase activity in S91 cells, whereas 1000 uM (1R,2R,3S,5R)-(−)-pinanediol was required for this same level of induction (Table 1). VI− was nearly as active as II+, inducing an 8-fold increase of tyrosinase at 100 uM (Table 1).

Melanogenic activity of this class of compounds is dependent on enantiomeric configuration, as demonstrated by the fact that II− and VI+ were much less potent than II+ and VI− (Table 1). The alcohol enantiomers (III− and III+) induced much less melanogenic than the most potent diols (II+ and VI−), substantiating our previous finding that alcohols are usually less potent inducers of melanogenesis than diols (Brown, et al., *J. Invest. Dermatol.* 110:428–437, and PCT/US98/05346).

The compounds of this invention result both in induction of cell cycle arrest and differentiation of S91 mouse melanoma cells, indicating that they have potential use as chemotherapeutic differentiation agents. It can be seen in Table 1, that following a 6 day treatment period, the compounds of this invention result in a reduction of cell numbers below that of untreated controls. However, the compounds of this invention are considered to be cytostatic (induce cell cycle arrest) rather than cytotoxic since: (i) they did not result in a reduction of cell number below the number originally plated ($0.05 \times 10^6$ viable cells/treatment), (ii) reductions of cell number relative to controls were accompanied by induction of the multipolar phenotype and induction of tyrosinase, both well-known markers of differentiation, and, (iii) there was no apparent detachment of cells from dishes as indicated by a lack of cells floating in the media. In contrast, 3-ethyl-2-aldehyde-pinane resulted in detachment of cells from dishes with little induction of markers of differentiation (Table 1).

Previously, we have found that monoterpene diols result in induction of melanogenesis in S91 mouse melanoma cells by stimulating the nitric oxide/cyclic GMP/protein kinase G signal transduction pathway (PCT/US98/05346). Thus, it is contemplated that the novel monoterpene diols of the present invention, will also induce melanogenesis by this same pathway. Since monoterpene diols that induced melanogenesis by the nitric oxide/cyclic GMP/protein kinase G pathway, also induced differentiation of neuronal cells (PCT/US98/05346), it is contemplated that the novel monoterpene diols of this invention will have a similar activity in neuronal cells. Furthermore, it is contemplated that the novel monoterpene diols of this invention will have the potential to treat diseases remedied by stimulation of the nitric oxide/cyclic GMP/protein kinase G as described for monoterpene diols in PCT/US98/05346. Thus, all of the uses described for monoterpene diols in PCT/US98/05346 are contemplated to apply to the compounds of the present invention.

EXAMPLE 7

Induction of tanning in human skin by (+)-2,2-dimethyl-3-hydroxy-3-hydroxymethyl-norbornanes (II+), and, (−)-2,2-dimethyl-3-(2,3-dihydroxy-propan-3-yl)-norbornanes (VI−)

Compounds of the present invention were formulated for application to human skin using compositions described in PCT/US98/05346 and co-pending application Serial No. filed Apr. 6, 1998 entitled "Dermatological Formulations and Methods", the contents of both of which are incorporated herein by reference. Each formulation contained 50% α-hydroxy acid (AHA) face cream (CVS generic containing 8% AHA; therefore final concentration of AHA in formulation was 4%), 35% isopropyl alcohol (Fisher), the indicated amounts of each compound (Table 2), and deionized water as required to bring the volume up to 100%. The vehicle control solution contained 50% AHA face cream, 35% isopropyl alcohol, and 15% deionized water. Ten ul of each formulation was applied twice per day for 10 days, followed by application of 10 ul once per day for the remainder of the application period. The treatment spots were along the anterior forearm which correspond to the region of the forearm closest to the body when at rest. The Vehicle control was closest the elbow and VI− was closest the wrist, with the other treatment spots along the arm in the order given in Table 2. The treated individual was Caucasian with an untanned (pale) forearm prior to treatment.

The degree of pigmentation was estimated each day prior to the first treatment, using a subjective rating system as follows: 0=no change from background; +0.25=slight darkening, indistinct; 0.5=slight darkening; +1=slight-moderate darkening; +2=moderate, even darkening; +3=substantial, even darkening; +4=profound, even darkening (from Brown, et al., 1998, J. Invest. Dermatol. 110:428–437). The following results were obtained:

TABLE 2

Pigmentation Ratings

| Treatment | Day 2 | 4 | 6 | 8 | 10 | 12 | 14 |
|---|---|---|---|---|---|---|---|
| Vehicle | 0 | 0 | 0 | 0 | 0 | 0 | 0 |
| 0.1M (2R,3S)-(−)-PD[1] | 0 | 0 | 0.25 | 0.25 | 0.25 | 0.25 | 0.25 |
| 0.25M (2R,3S)-(−)-PD | 0 | 0 | 0.25 | 0.75 | 1.0 | 1.0 | 1.0 |
| 1.0M (2R,3S)-(−)-PD | 0 | 0 | 0.5 | 0.75 | 1.0 | 1.5 | 1.5 |
| 0.1M (1R)-2,3-c/e-BD[2] | 0 | 0 | 0.25 | 0.75 | 1.0 | 1.5 | 1.5 |
| 0.1M II+[3] | 0 | 0.25 | 0.5 | 0.5 | 1.0 | 1.25 | 1.25 |
| 0.1M VI−[4] | 0 | 0 | 0.5 | 0.5 | 1.0 | 2.0 | 2.5 |

Figure 1:
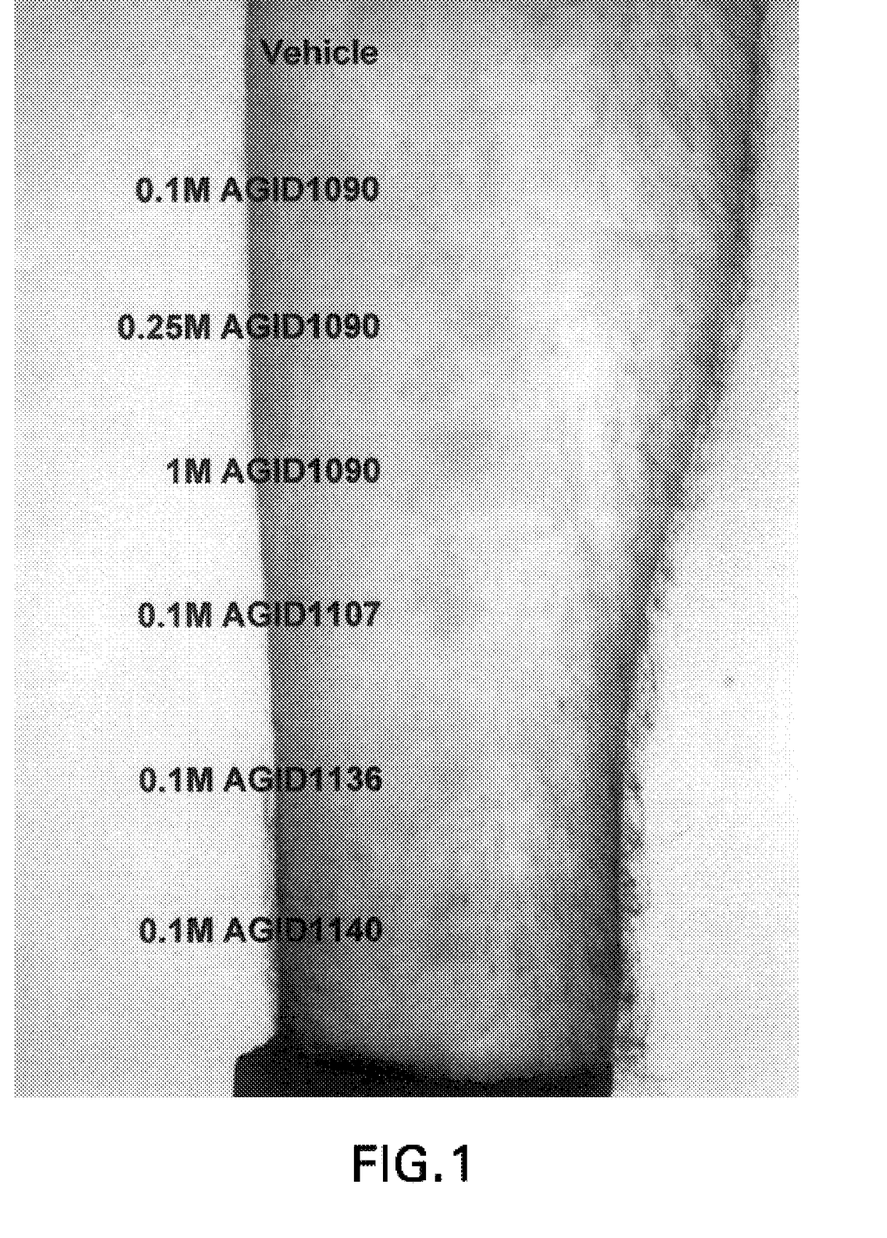
FIG. 1 is a photograph of treated human skin as described in Example 7.

[1](2R,3S)-(−)-PD: (1R,2R,3S,5R)-(−)-pinanediol
[2](1R)-2,3-c/e-BD: (1R)-2,3-cis/exo-bornanediol
[3]II+: (+)-2,2-dimethyl-3-hydroxyl-3-hydroxymethyl-norbornane
[4]VI−: (−)-2,2-dimethyl-3-(2,3-dihydroxyl-propan-3-yl)-norbornane See also FIG. 1, which is a photograph of the subject skin taken on day 14.

Results show that II+ and VI− were 5- and 10-fold more potent, respectively, than (2R,3S)-(−)-PD with regards to induction of tanning when applied to human skin (compare 14 day 0.1M treatment results in Table 2). Thus, results for induction of melanogenesis in human skin by these compounds (Table 2) parallel those for induction of melanogenesis in cell culture (Table 1). However, (1R)-2,3-c/e-BD which was only about 2-fold more potent than (2R,3S)-(−)-PD in cell culture (see Table 20 in PCT/US98/05346), was 5-fold more potent when applied to human skin (compare 14 day 0.1M treatment results in Table 2). Some of these differences may be related to the ability of individual compounds to penetrate human skin, a property that is relatively unimportant in cell culture tests. In this regard, it is interesting to note that even though II+ and VI− exhibit nearly identical melanogenic potency in cell culture (Table 1), by day 14, VI− has resulted in approximately twice as much skin pigmentation as II+ (Table 2). However, unlike pure II+ which is a crystalline substance, pure VI− is a liquid; this is a property that is known to highly favor skin penetration (Barry, B. W. 1983. Dermatological Formulations: Percutaneous Absorption, Marcel Dekker, Inc., New York, p. 480). Thus, the ability of compounds to induce tanning in human skin is likely to depend not only on their intrinsic melanogenic activity, but also on their ability to penetrate skin. Given these findings, VI− [(−)-2,2-dimethyl-3-(2,3-dihydroxy-propan-3-yl)-norbornane] is a preferred compound for incorporation into cosmeceutical tanning formulations.

Part of the rationale for the design of VI− [(−)-2,2-dimethyl-3-(2,3-dihydroxy-propan-3-yl)-norbornane] was to produce a structural analog of tetrahydrobiopterin that presented a protruding propanediol side chain similar to tetrahydrobiopterin. Additionally, the seminal discovery in this series of inventions was that 1,2-propanediol (propylene glycol) induces melanogenesis, and most additional compounds of these inventions contain propylene glycol embodied within their structures. Tetrahydrobiopterin is a necessary co-factor for induction of nitric oxide synthase and resultant nitric oxide synthesis. The family of compounds embodied by this invention and related inventions are thought to exert their effects via the nitric oxide signal transduction pathway (discussed above). Therefore, it is contemplated that the relatively high potency of VI− may be related, in part, to its structural similarity to tetrahydrobiopterin with regards to a protruding propanediol substituent group.

What is claimed is:

1. A compound selected from the group consisting of:
   (a) (−)-2,2-dimethyl-3-hydroxy-3-hydroxymethyl-norbornane;
   (b) derivatives of (−)-2,2-dimethyl-3-hydroxy-3-hydroxymethyl-norbornane;
   (c) (+)-2,2-dimethyl-3-hydroxy-3-hydroxymethyl-norbornane;
   (d) derivatives of (+)-2,2-dimethyl-3-hydroxy-3-hydroxymethyl-norbornane;
   (e) (−)-2,2-dimethyl-3-(2,3-dihydroxy-propan-3-yl)-norbornane;
   (f) derivatives of (−)-2,2-dimethyl-3-(2,3-dihydroxy-propan-3-yl)-norbornane;
   (g) (+)-2,2-dimethyl-3-(2,3-dihydroxy-propan-3-yl)-norbornane; and
   (h) derivatives of (+)-2,2-dimethyl-3-(2,3-dihydroxy-propan-3-yl)-norbornane.

2. A topical formulation comprising at least one compound of claim 1 and an acceptable carrier.

3. A compound selected from the group consisting of:
   (a) (−)-2,2-dimethyl-3-hydroxy-3-hydroxymethyl-norbornane;
   (b) derivatives of (−)-2,2-dimethyl-3-hydroxy-3-hydroxymethyl-norbornane;
   (c) (+)-2,2-dimethyl-3-hydroxy-3-hydroxymethyl-norbornane; and
   (d) derivatives of (+)-2,2-dimethyl-3-hydroxy-3-hydroxymethyl-norbornane.

4. A topical formulation comprising at least one compound of claim 3 and an acceptable carrier.

5. A compound selected from the group consisting of:
   (a) (+)-2,2-dimethyl-3-hydroxy-3-hydroxymethyl-norbornane; and
   (b) derivatives of (+)-2,2-dimethyl-3-hydroxy-3-hydroxymethyl-norbornane.

6. A topical formulation comprising at least one compound of claim 5 and an acceptable carrier.

7. A compound selected from the group consisting of:
   (a) (−)-2,2-dimethyl-3-(2,3-dihydroxy-propan-3-yl)-norbornane;
   (b) derivatives of (−)-2,2-dimethyl-3-(2,3-dihydroxy-propan-3-yl)-norbornane;
   (c) (+)-2,2-dimethyl-3-(2,3-dihydroxy-propan-3-yl)-norbornane; and
   (d) derivatives of (+)-2,2-dimethyl-3-(2,3-dihydroxy-propan-3-yl)-norbornane.

8. A topical formulation comprising at least one compound of claim 7 and an acceptable carrier.

9. A compound selected from the group consisting of:
   (a) (−)-2,2-dimethyl-3-(2,3-dihydroxy-propan-3-yl)-norbornane; and
   (b) derivatives of (−)-2,2-dimethyl-3-(2,3-dihydroxy-propan-3-yl)-norbornane.

10. A topical formulation comprising at least one compound of claim 9 and an acceptable carrier.

11. A method for the stimulation of melanogenesis in mammalian skin, hair, wool or fur, which comprises administering to a locus in need of such stimulation an effective amount of at least one compound of claim 1.

12. A method for the treatment of proliferative, tumorous or cancerous disorders in mammals, which comprises administering to a mammal in need of such treatment an effective amount of at least one compound of claim 1.

13. The method of claim 12 wherein the disorder is selected from the group consisting of actinic keratosis, basal cell carcinoma, squamous cell carcinoma, fibrous histiocytoma, dermatofibrosarcoma protuberans, hemangioma, nevus flammeus, xanothoma, Kaposi's sarcoma, mastocytosis, mycosis fungoides, lentigo, nevo-cellular nevus, lentigo maligna, malignant melanoma, metastatic carcinoma, psoriasis vulgaris, psoriasis eosinophilia, acne vulgaris, acne conglobata, acne fulminans, osteoma cutis, nodulocystic acne, and cystic acne.

14. A method for the treatment of neurodegenerative disorders or nerve damage in mammals, which comprises administering to a mammal in need of such treatment an effective amount of at least one compound of claim 1.

15. A method according to claim 14, wherein the treatment reverses neuronal damage.

16. A method according to claim 14, wherein the treatment alleviates a neurodegenerative disease.

17. A method according to claim 16, wherein the disease is selected from the group consisting of Parkinson's disease, amyotrophic lateral sclerosis, Alzheimer's disease, diffuse cerebral cortical atrophy, Lewy-body dementia, Pick disease, mesolimbocortical dementia, thalamic degeneration, Huntington chorea, cortical-striatal-spinal degeneration, cortical-basal ganglionic degeneration, cerebrocerebellar degeneration, familial dementia with spastic paraparesis, polyglucosan body disease, Shy-Drager syndrome, olivopontocerebellar atrophy, progressive supranuclear palsy, dystonia musculorum deformans, Hallervorden-Spatz disease, Meige syndrome, familial tremors, Gilles de la Tourette syndrome, acanthocytic chorea, Friedreich ataxia, Holmes familial cortical cerebellar atrophy, Gerstmann-Straussler-Scheinker disease, progressive spinal muscular atrophy, progressive balbar palsy, primary lateral sclerosis, hereditary muscular atrophy, spastic paraplegia, peroneal muscular atrophy, hypertrophic interstitial polyneuropathy, heredopathia atactica polyneuritiformis, optic neuropathy, and ophthalmoplegia.

18. A method of treating a disease regulated by the nitric oxide/cyclic GMP/protein kinase G pathway in mammals which comprises administering to a mammal in need of such treatment an effective amount of at least one compound of claim 1.

19. The method of claim 18, wherein the treated disease is selected from the group consisting of heart disease, hypertension, stroke, chronic obstructive pulmonary disease, adult respiratory distress syndrome, microvascular functional abnormalities in diabetes, hemostatic irregularities of glomerular vascular and tubular function, microvascular irregularities in the liver, disorders of bladder function and reflex relaxation for micturition, disorders of neurotransmitter release, neuron morphogenesis, synaptic plasticity, and neuroendrocrine regulation, migraine headaches, benign anal disease, and impotence.

* * * * *